US00PP25529P3

(12) United States Plant Patent
Bright

(10) Patent No.: US PP25,529 P3
(45) Date of Patent: May 12, 2015

(54) HYBRID TEA ROSE PLANT NAMED 'IRB0182G'

(50) Latin Name: *Rosa hybrida*
Varietal Denomination: IRB0182G

(71) Applicant: Laura Rose Bright, Richmond, IN (US)

(72) Inventor: Laura Rose Bright, Richmond, IN (US)

( * ) Notice: Subject to any disclaimer, the term of this patent is extended or adjusted under 35 U.S.C. 154(b) by 92 days.

(21) Appl. No.: 13/694,196

(22) Filed: Nov. 6, 2012

(65) Prior Publication Data

US 2014/0130216 P1 May 8, 2014

(30) Foreign Application Priority Data

Nov. 1, 2012 (EC) ..... 1162-12

(51) Int. Cl.
*A01H 5/00* (2006.01)

(52) U.S. Cl.
USPC ..... Plt./130

(58) Field of Classification Search
USPC ..... Plt./130, 132, 134
See application file for complete search history.

*Primary Examiner* — Kent L Bell

(74) *Attorney, Agent, or Firm* — Foley & Lardner LLP; Benjamin A. Berkowitz

(57) ABSTRACT

A new and distinct variety of Hybrid Tea rose plant named 'IRB0182G' characterized by its upright, freely branching growth habit that will produce basal breaks and branches from pinched plants, yellow inner petal color, and yellow-green outer petal and closed petal color.

5 Drawing Sheets

Figure 1:
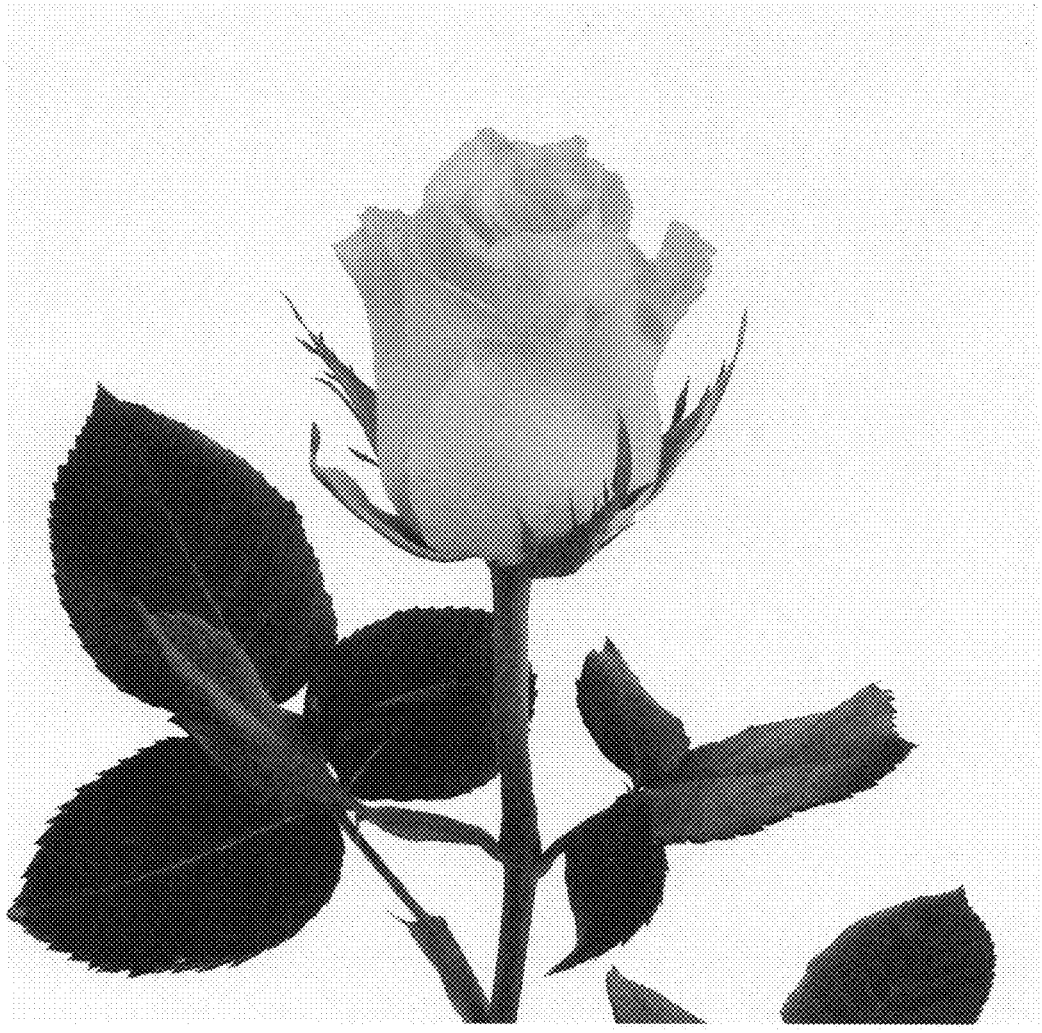

Latin name of the genus and species of the plant claimed: *Rosa hybrida* Hybrid Tea Rose.

Variety denomination: 'IRB0182G'.

BACKGROUND OF THE INVENTION

The present invention relates to a new and distinct Hybrid Tea cultivar of Rose plant, botanically known as *Rosa hybrida*, hereinafter referred to by the cultivar name 'IRB0182G'.

The new Hybrid Rose 'IRB0182G' is a product of a breeding program conducted by the inventor, Laura Rose Bright, in Richmond, Ind., USA. The new cultivar that is from the cross of two proprietary, unpatented seedlings, *Rosa hybrida* selection identified as code number 19-85W, a white seedling, as the female parent and *Rosa hybrida* selection identified as code number 92-177Y as the male parent, reproduces true-to-type. The cross was made with a small paint brush using pollen from the male parent applied to the stigma on the female parent. Once the rose hip formed with the seeds from the crossing inside the hip, it was allowed to mature on the plant. The seeds were then collected from the rose hip and dried. The seeds were then sent to Bogota, Colombia via courier. The seed was germinated in the savannah area north of Bogota, Colombia, and the initial selection of the seedling was made in the same location. The initial selected only involves looking at the basic characteristics such as number of petals, color, foliage, and other basic observations that can be made on the small plants that come from the seeds that germinate. The new hybrid rose, 'IRB0182G', was considered to have the basic characteristics to warrant further evaluation. Asexual reproduction of the new hybrid rose 'IRB0182G' is performed by grafting and was first performed in 2003 in the savannah area north of Bogota, Colombia. Propagation through patch budding has demonstrated that the combination of characteristics as herein disclosed for the new cultivar are firmly fixed and retained through successive generations of asexual reproduction. After this initial selection, a limited quantity of plants were reproduced asexually and sent to Quito, Ecuador. With the small quantity of plants initially propagated in the savannah area north of Bogota, it was not possible to do the complete initial commercial evaluation to determine if the cultivar should be offered to the commercial trade. Therefore, the commercial selection was made in the Valle de los Chillos southeast of Quito, Ecuador. The commercial selection involved expanding the quantity of plants to a quantity of over 300, and handling the plants using normal cultural practices to evaluate productivity, stem length, head size, cycle times, vase life of cut flowers, observations of potential commercial customers in the test area who observed the plant at this phase of evaluation, and other requirements to decide if the variety should be introduced commercially.

BRIEF DESCRIPTION OF THE PHOTOGRAPHS

The accompanying photographs illustrate the overall appearance of the new Hybrid rose 'IRB0182G' showing the colors as true as is reasonably possible with colored reproductions of this type. Color references are from The Royal Horticultural Society Colour Chart (R.H.S.) digital version available on the web page address: rhscf.orgfree.com. Colors in the photographs may differ slightly from the color values cited in the detailed botanical description which accurately describes the color of 'IRB0182G'.

Figure 2:
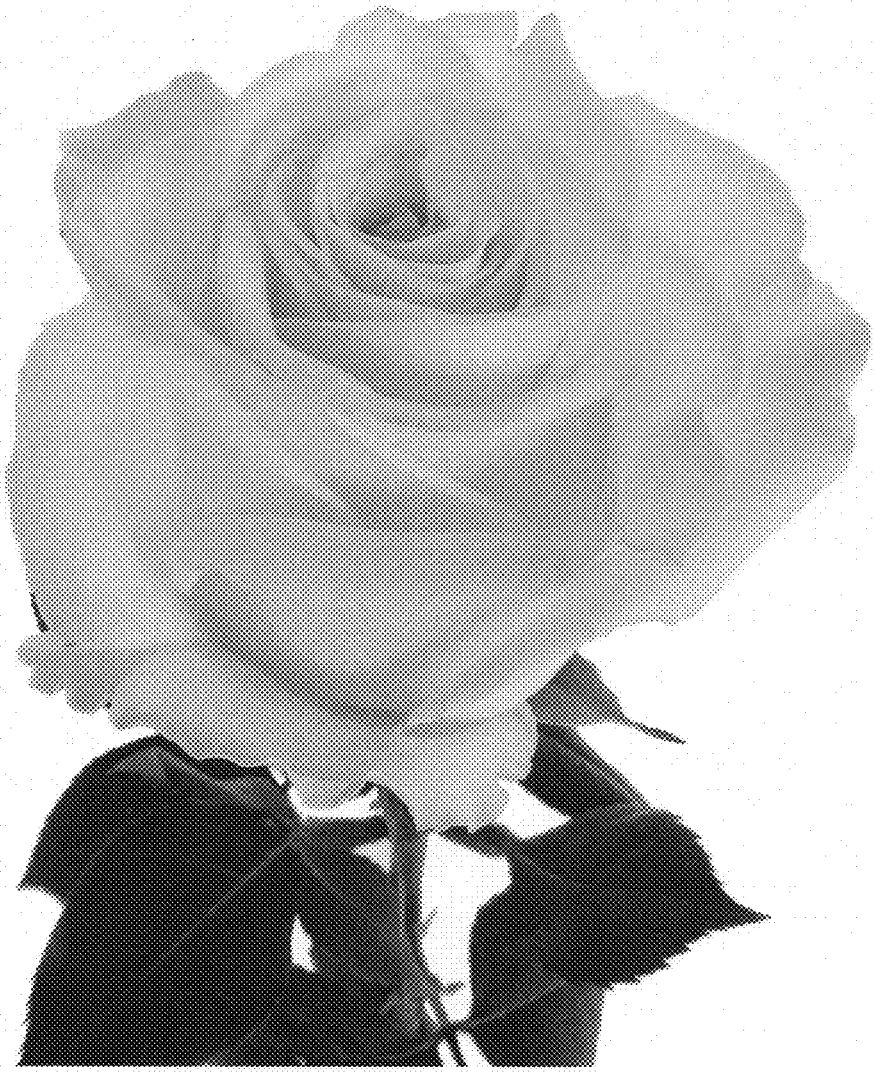
Figure 3:
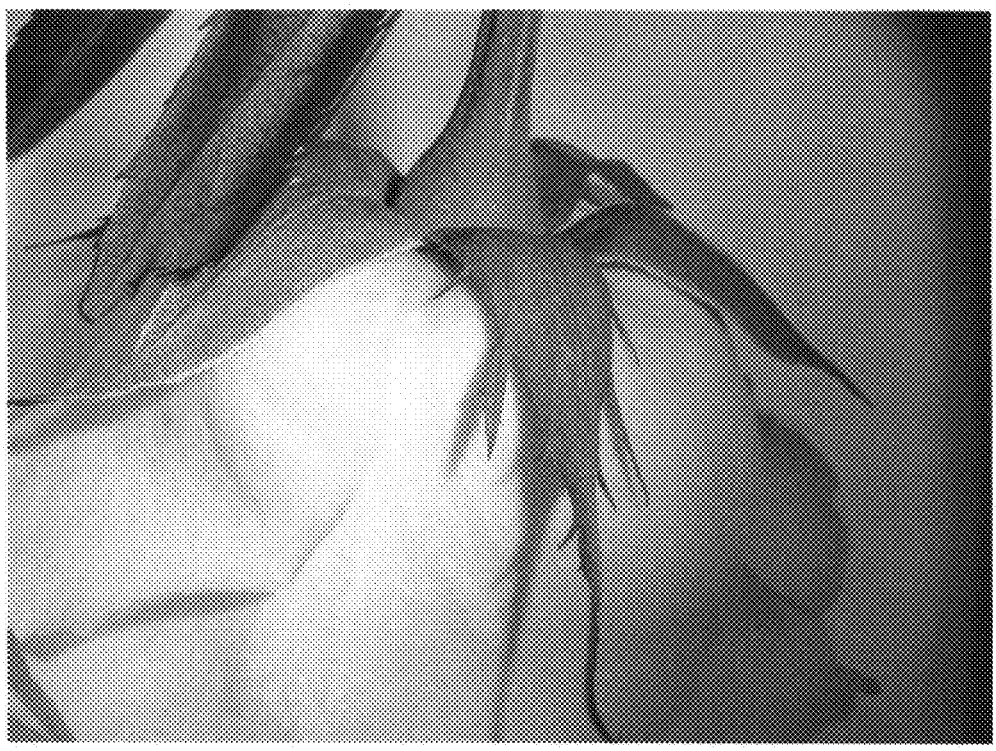
Figure 4:
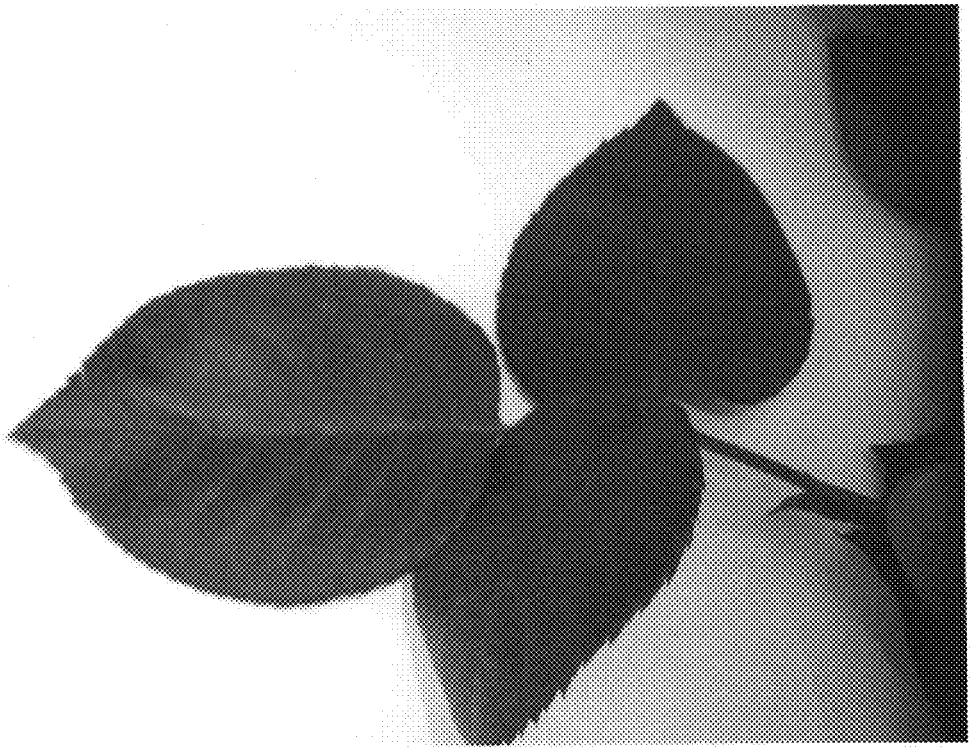
Figure 5:
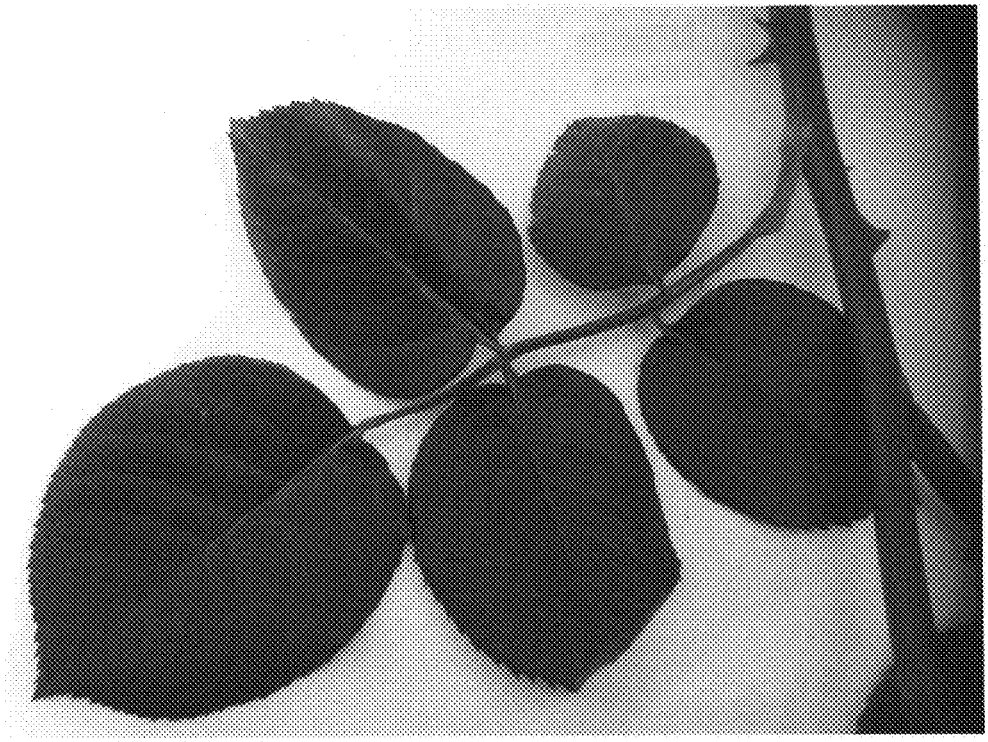

FIG. 1 shows a flower, sepals, and foliage of 'IRB0182G'.
FIG. 2 shows a close-up view of a flower of 'IRB0182G'.
FIG. 3 shows a close-up view of the sepals of 'IRB0182G'.
FIG. 4 shows a petiole of 'IRB0182G' with three leaflets.
FIG. 5 shows a petiole of 'IRB0182G' with five leaflets.

DETAILED BOTANICAL DESCRIPTION

Plants of the cultivar 'IRB0182G' have not been observed under all possible environmental conditions. The phenotype may vary somewhat with variations in environment such as temperature and light intensity which can vary by season, without, however, any variance in genotype. The photographs and following observations and measurements describe plants grown in Cayambe, Pichincha, Ecuador, under commercial practice in a polyethylene plastic with UV filter covered greenhouse in a climate where the night temperatures may drop as low as 2 C but typically reach about 8 C and night and may rise to around 31 C but typically reach around 21 C day temperatures. The location is about 2850 meters above sea level and less than 2 km north of the equator. The observations are from plants over one year old that were propagated by patch budding on a 'Natal Brier' rose rootstock.

Botanical classification: *Rosa hybrida* hybrid tea rose.

Parentage:

*Female parent*.—Proprietary *Rosa hybrida* selection identified as code number 19-85W, a white seedling, not patented.

*Male parent*.—Proprietary *Rosa hybrida* selection identified as code number 92-177Y a yellow seedling, not patented.

Propagation: Although the cultivar can be propagated from a rooted cutting, it is recommended that it be budded on a suitable rootstock such as *Rosa hybrida* var. 'Manetti' or 'Natal Brier' for greenhouse production of roses. The grafting can be as a bud, t graft, stentling or other type of graft. The rootstocks for budded plants should generally be grown for several weeks if the grafting is in the greenhouse for the plant to be actively growing to accept the bud.

*Rooting habit*.—Will depend upon the rootstock used.

Plant:

*General appearance*.—The cultivar 'IRB0182G' is a upright, freely branching grower that will produce both basal breaks and branches from the pinched plants. Although generally grown using a system with posts and wire or string guides, the observed and typical plant growth habit does not require any special treatment to insure a primarily vertical growth habit.

*Plant height, lateral branches, stems and internodes*.—Typically, the plant will be managed with the flower cutting points between 30 cm and 150 cm. Lateral branches will generally be from 40 to 80 cm in length, with a diameter of approximately 1 cm in the lower area, 0.6 to 0.7 cm in the middle area of the stem and 0.4 to 0.6 cm at the peduncle. Internode length is generally from 4.0 to 7.0 cm and the stem texture is smooth. The color of the branches approaches RHS Green 134A.

*Plant diameter*.—The plant will generally be managed with a diameter up to 30 cm.

*Thorns* (*or prickles since they are outgrowths of the epidermis*).—Reddish brown color, similar to RHS 169A in color, up to about 12 cm from the base of the flower. The thorns under normal growing conditions are about 1 cm long. In the area of the stems that has thorns, under normal growing conditions there are normally between 12 and 13 thorns in a 25 cm long stem section.

*Leaves and leaflets*.—The leaves of the cultivar are arranged in an odd pinnate compound form, often with seven leaflets in the lower part of a lateral branch, and then with five leaflets in the middle of the branch, and upper two leaves generally have three leaflets. Color is generally similar to The Royal Horticultural Society Yellow Green group color 147A on the top of the leaflets and 144A on the lower surface of the leaflets. The foliage is semi-glossy. The leaflets have a pinnate venation, a slightly serrated margin pointing toward the apex and an oval tending toward an aristate shape. The leaves with seven leaflets have a range of lengths of 11 to 16 cm and a width of 6 to 11 cm; with a leaflet length of 3 to 6 cm and a leaflet width of 2 to 4 cm. In some cases, the petiolule of the terminal leaflet is at a 45 degree angle from the rachis. The leaves with five leaflets have a leaf length of 20 to 22 cm, a leaf width of 14 to 16 cm, a leaflet length of 6 to 8 cm and a leaflet width of 4 to 6 cm. The second set of leaves below the flower have a leaf length of 14 to 16 cm, a leaf width of 11 to 12 cm, a terminal leaflet length of 8 to 9 cm and a lateral leaflet length of 6 to 7 cm. In some cases, the top leaf has a stipule that extends almost the complete length of the petiole with a leaf length of 8 to 9 cm and a width of 4 to 5 cm. In some cases there is a single leaflet near the top of the stem below the peduncle with a strap-like shape.

*Petioles*.—The petioles are generally 3 to 6 cm in length, approximately 2 mm in diameter with a color similar to RHS Green 143A.

*Rachis*.—The rachis is generally 7 to 9 cm long, approximately 2 mm in diameter with a color similar to RHS Green 143A.

*Stipules*.—The stipules are persistent adnate stipules with the base of the petiole. The shape of the stipules is scale-like, with one on each side of the petiole, a smooth margin, a typical length of approximately 3 cm, a width at the tip between the stipules on both sides of the petiole of about 1.5 cm and a width at the lower part of the stipules of approximately 5 mm. The color on the upper side of the stipules is similar to RHS Green 147A.

*Cut flowers*.—The cut flowers are very long lasting, with vase life of the cut flowers often around three weeks if properly handled, with a flower life on the plant similar to the vase life and with a long vase life of over two weeks in the case of shipments to distant markets when the proper post-harvest care is provided. The cut flowers will generally have a stem length from 40 cm to 80 cm depending upon growing conditions, if the cutting is going up or down on the plant, etc.

*Flower size*.—Flower bud height is generally from 5 to 6.5 cm at cut point. A mature flower with the sepals still up has a diameter of about 4 cm. A flower with an open cut point has a diameter of 5 to 7 cm. Open flower diameter generally ranges from 9 to 13 cm.

*Shape*.—Inner rows of petals form comparatively flat surface area with all the petals at approximately the same height.

*Color*.—Inner petal color of both surfaces of open flowers is generally similar to The Royal Horticultural Society Yellow Group 11B color. The predominant color of the outer petals and top of petals of closed flowers is generally similar to The Royal Horticultural Society Yellow-Green Group 145A. With the exception of the upper section of the inner side of the outer petals, the typical color is similar to RHS Yellow group 11B. Under colder growing condition or slightly lower light conditions, the green may be intensified. The color is greener in closed than open flowers.

*Petals*.—The margin of the outer petals is slightly undulating, while the inner petals have a smooth margin and a shape comes to a point. The base is between truncate and rounded in both cases. The open flower can have a flower depth of around 7 cm, but generally the flowers do not open to the point where the stamens and pistil are visible. An outer petal in a mature flower with the sepals still upright has a length of about 6 cm and a width of about 7 cm. Inner petals are about 5 mm smaller in each dimension. Petals on open flowers can reach 7 cm in length and 9 cm in width. The texture of the inner petals shows some veins, and slightly more venation is visible on the outer surface of the petals, but in neither case in the venation prominent or particularly visible, with the exception of the center vein on the outside of the outer petals on open flowers which can be seen from below the flower.

*Sepals*.—The five sepals are narrow near the tip, approximately 4 to 5 cm long under normal conditions, nearly 1 cm wide and have around six pairs of leaf-like extensions on each side. The upper side of the sepal is a lighter green than the lower side, with colors similar to RHS Greens 144B and 143A, respectively. Both surfaces are smooth with a prominent vein running the length of the lower surface.

*Peduncles*.—Peduncle is a green that approaches RHS Green 134A like the stem. The length is 6 to 8 cm and the diameter is 4 to 6 mm.

Flowering season: The plant flowers year-round on a continual basis under greenhouse conditions.

Reproductive organs: None observed, but a rose hip would be produced if the flower were allowed to pollinate and the fruit be allowed to form.

Receptacle: The urn shaped receptacle is approximately 1 cm in diameter, 1 cm in height and has a color similar to RHS Green 134A.

Seed/fruit: None observed

Disease and pest resistance: Normal, with some susceptibility to *Botrytis cinerea*.

Comparative varieties: The two most common roses with similar colors are *Rosa hybrida* 'Kornalist' (unpatented) which is also a yellow-green but has a smaller flower and shorter stem, and *Rosa hybrida* 'Tanedaj' (unpatented) which has a smaller flower and is cream-green in color.

What is claimed is:

1. A new and distinct variety of Hybrid tea rose plant named 'IRB0182G', as herein illustrated and described by the characteristics set forth above.

* * * * *